(12) United States Patent
Gray

(10) Patent No.: US 8,541,226 B2
(45) Date of Patent: Sep. 24, 2013

(54) BIOREACTOR FOR MESOPHILIC AND/OR THERMOPHILIC FERMENTATION

(75) Inventor: Vincent Myles Gray, Johannesburg (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 281 days.

(21) Appl. No.: 12/676,643

(22) PCT Filed: Sep. 9, 2008

(86) PCT No.: PCT/IB2008/002331
§ 371 (c)(1), (2), (4) Date: Mar. 5, 2010

(87) PCT Pub. No.: WO2009/034439
PCT Pub. Date: Mar. 19, 2009

(65) Prior Publication Data
US 2010/0304420 A1    Dec. 2, 2010

(30) Foreign Application Priority Data
Mar. 15, 2007  (ZA) .................................. 2007/02170

(51) Int. Cl.
*C12M 1/00*  (2006.01)
*C12N 1/02*  (2006.01)

(52) U.S. Cl.
USPC ..... 435/261; 435/252; 435/252.1; 435/252.4; 435/289.1; 435/308.1; 435/290.4

(58) Field of Classification Search
None
See application file for complete search history.

(56) References Cited

FOREIGN PATENT DOCUMENTS

| WO | 2005/042694 A2 | 5/2005 |
|---|---|---|
| WO | 2007/021773 A2 | 2/2007 |
| WO | 2007/090138 A2 | 9/2007 |

OTHER PUBLICATIONS

International Preliminary Report on Patentability for PCT/IB2008/002331 dated Mar. 16, 2010.
International Search Report for PCT/IB2008/002331 date Oct. 15, 2009.

*Primary Examiner* — James Martinell
(74) *Attorney, Agent, or Firm* — Nixon Peabody LLP

(57) ABSTRACT

This invention relates to a bioreactor for producing high rates of hydrogen from plant biomass. It also relates to the rapid screening, selection and isolation of biofilm forming mesophilic and/or thermophilic bacteria or bacteria consortia that generate high levels of hydrogen from plant biomass or from soluble hydrolysates derived from the hydrolysis of cellulosic materials including hemicellulose. The reactor comprises a primary reactor vessel having a bed of hydrogen producing bacteria towards its base located within a secondary reactor vessel which functions as a hydrogen gas collector and as a clarifier and separator. The plant biomass may be one or a mixture of insoluble cellulosic material and a hydrolysate derived from hydrolysis of cellulosic material. In one embodiment the bed of the primary reactor vessel is fluidised by recycling hydrogen gas saturated plant biomass effluent from the secondary reactor vessel to the primary reactor vessel.

44 Claims, 2 Drawing Sheets

BIOREACTOR FOR MESOPHILIC AND/OR THERMOPHILIC FERMENTATION

CROSS REFERENCE TO RELATED APPLICATIONS

Figure 1:
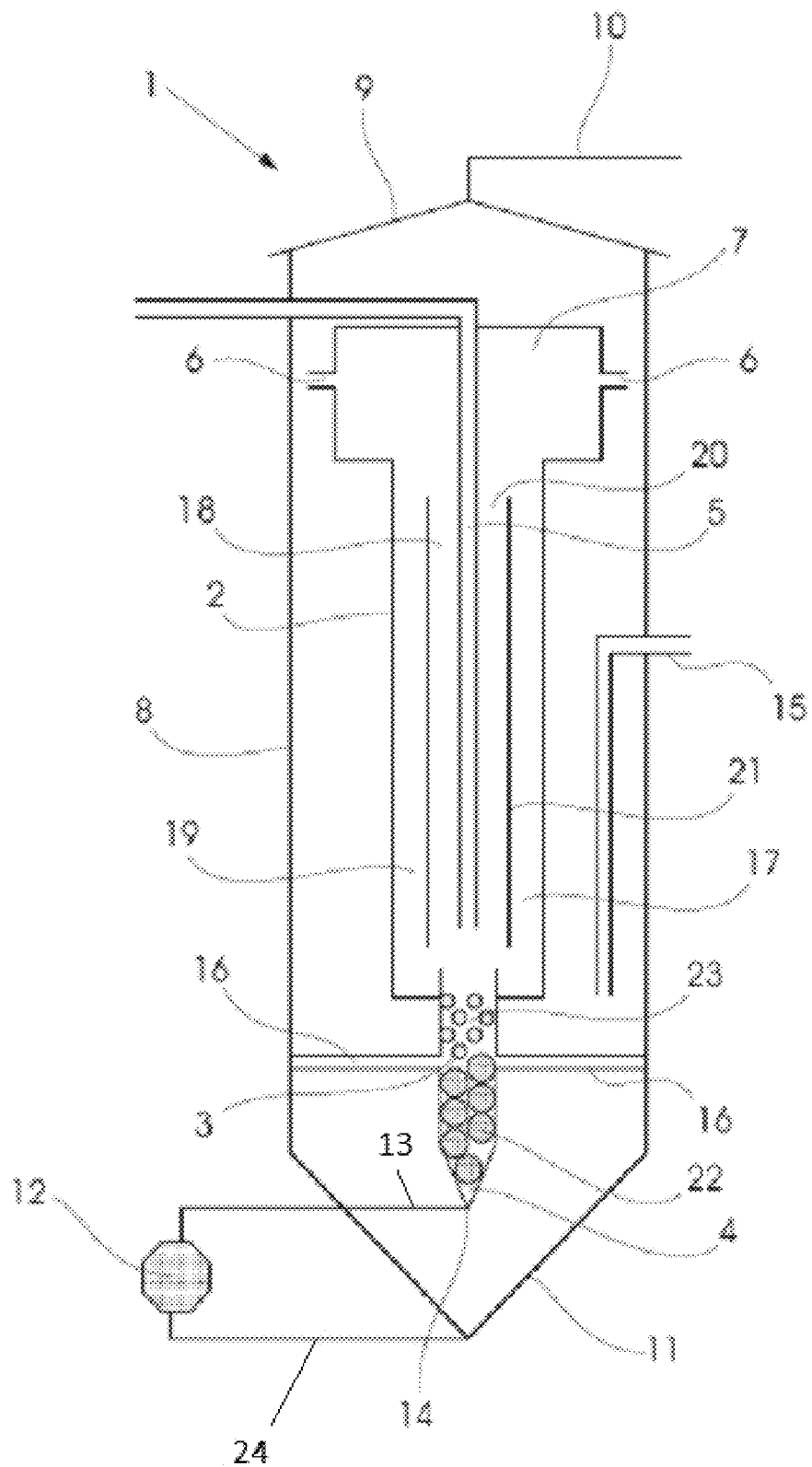

This application is a national stage application under 35 U.S.C. §371 from PCT Application No. PCT/IB2008/002331 filed Sep. 9, 2008, claiming priority to South African Application No. 2007/02170 filed Sep. 15, 2007.

FIELD OF THE INVENTION

This invention relates to bioreactor for the production of high rates of hydrogen from plant biomass and for the rapid screening, selection and isolation of biofilm forming mesophilic and/or thermophilic bacteria or bacteria consortia that generate high levels of hydrogen from plant biomass or from soluble hydrolysates derived from the hydrolysis of cellulosic materials including hemicellulose.

BACKGROUND TO THE INVENTION

Increasing prices of fossil fuels and petroleum products has, to a large extent, resulted in the production of hydrogen and ethanol, as well as other fermentation products, from plant biomass becoming an increasingly attractive option for alternative fuel production. The production of such alternative fuels is also important for countries that lack oil or coal.

In addition, hydrogen is recognized as a clean and recyclable energy carrier. Consequently it is considered to be one of the major energy sources in the future and much effort has been expended on exploring methods of sufficiently and efficiently supplying hydrogen. Furthermore, biological production of hydrogen from organic wastes as well as from other recyclable resources is considered preferable to the production of hydrogen from food crops for, while the hydrogen yield of food crops such as maize and wheat is relatively high, there is a global food shortage which is in danger of becoming exacerbated by the use of food crops in biological hydrogen producing reactors.

Currently no suitable bioreactor apparatus or methodology is known to the inventor for the rapid screening, selection and isolation of biofilm, floc and granule forming thermophilic bacteria or bacteria consortia that generate high levels of hydrogen from plant biomass including the soluble hydrolysates derived from the hydrolysis of cellulosic materials and particularly of cellulosic materials such as sugar cane waste and effluent that been subjected to only minimum pretreatment such as milling and wet heating.

Thermophiles, including extreme thermophiles, have many advantages as agents for the generation of biohydrogen from cellulose and from soluble hydrolysate derived from cellulose hydrolysis. Perhaps their main advantage is that high temperatures exclude microbial contamination from a bioreactor system. High temperature also shift the equilibrium constant for the hydrogen generating reactions in the forward direction thereby increasing the hydrogen yield. Most thermophiles and extreme thermophiles are, however, difficult to culture and maintain as pure cultures although it has been found that the hydrolysis of cellulosic materials and the generation of hydrogen from the products of this hydrolysis becomes increasingly favourable under the action of a mixed consortium of bacteria that includes anaerobic cellulolytic bacterial species.

OBJECT OF THE INVENTION

It is an object of this invention to provide a bioreactor for the production of high rates of hydrogen from plant biomass and for the rapid screening, selection and isolation of biofilm forming thermophilic bacteria or bacteria consortia that generate high levels of hydrogen from plant biomass or from soluble hydrolysates derived from the hydrolysis of cellulosic materials including hemicellulose.

SUMMARY OF THE INVENTION

In accordance with this invention there is provided a bioreactor for producing hydrogen from plant biomass, the reactor comprising a primary reactor vessel having a bed of, hydrogen producing bacteria towards its base, a plant biomass inflow, a treated plant biomass effluent outflow towards its operatively upper end, and a gas saturated plant biomass effluent recycle inlet into the bed, and a secondary reactor vessel having a treated plant biomass effluent inlet from the primary reactor vessel, a gas outlet and a gas saturated plant biomass effluent recycle outlet, the gas saturated plant biomass effluent recycle outlet leading to a recirculation pump which, in use, recycles gas saturated plant biomass effluent from the secondary reactor vessel to the primary reactor vessel.

There is further provided for the bed to be a fluidised bed, alternatively a settled bed, further alternatively a, expanded bed and, in the case of a fluidised bed, for recycled gas from the secondary reactor vessel to the primary reactor vessel to fluidize the bed of hydrogen producing bacteria in the primary reactor vessel.

There is further provided for the bacteria to be mesophilic and/or thermophilic bacteria.

There is also provided for the recycled plant biomass effluent to be saturated with hydrogen gas produced in the primary reactor vessel.

There is further provided for the bed of hydrogen producing bacteria to have at least one inorganic nutrient feed inlet.

There is also provided for the primary reactor vessel to be located within the secondary reactor vessel, for the secondary reactor vessel to have an excess, unrecycled plant biomass effluent outlet and for the secondary reactor vessel to function, in use, as a clarifier and/or gas separator for treated plant biomass effluent received from the primary reactor vessel.

There is also provided for the hydrogen producing bacteria to be a mixed consortium of mesophylic bacteria that includes anaerobic cellulolytic bacteria; for the bacteria making up the mixed consortium to be selected from one or more of a range of mesophylic habitats including primary sewage, soils, compost and rumen dung; and for the hydrogen producing bacteria to be adapted to temperatures ranging from between 20° C. to 80° C. and preferably between 25° C. to 75° C.

There is further provided for the treated plant biomass to be insoluble, preferably cellulosic plant material that has been subjected to only minimum pretreatment being milling and/or wet heating, alternatively for the treated plant biomass to be a soluble hydrolysate derived from hydrolysis of cellulosic material, further alternatively a mixture of insoluble cellulosic material and a hydrolysate derived from hydrolysis of cellulosic material.

There is also provided for the primary reactor vessel to have a base from which the bed is formed in use, for the bed to be formed by a particulate material bed overlaid with activated carbon particles, for the particulate material of the bed to be formed by one or more of steel balls, gravel, glass beads, coal ash particles and the like, and for the particulate material of the bed to be coated with a biofilm formed from a mixed consortium of thermophilic and/or mesophylic bacteria.

Further features of the invention provide for the primary reactor vessel to have a circulation means for circulating partially treated plant biomass within the reactor vessel, the circulation means comprising a draft tube through which gas saturated material is directed from the reactor base upwardly and a downward tube through which partially treated biomass flowing from an outlet to the draft tube is returned to the reactor base.

The invention extends to a method for producing hydrogen from plant biomass comprising the following steps:
a) introducing a plant biomass into a primary reactor vessel of a bioreactor as described above having a bed of hydrogen producing bacteria towards its base:
b) treating the introduced plant biomass with a mixed consortium of hydrogen producing bacteria that includes anaerobic cellulolytic bacteria to produce hydrogen;
c) transferring the treated plant biomass to a secondary reactor vessel having a treated plant biomass effluent inlet from the primary reactor vessel;
d) collecting hydrogen gas from the second reactor vessel and clarifying treated plant biomass effluent;
e) collecting a supernatant from the clarified treated plant biomass; and
f) recirculating uncollected clarified treated plant biomass to the primary reactor vessel.

There is also provided for the recycled plant biomass effluent to be saturated with hydrogen gas produced in the primary reactor vessel.

There is further provided for the bed to be a fluidised bed, alternatively a settled bed, further alternatively a, expanded bed and, in the case of a fluidised bed, for recycled gas from the secondary reactor vessel to the primary reactor vessel to fluidize the bed of hydrogen producing bacteria in the primary reactor vessel.

There is further provided for the bacteria to be mesophilic and/or thermophilic bacteria.

There is further provided for introducing at least one inorganic nutrient feed into the bed of hydrogen producing bacteria.

Further features of the invention provide for circulating partially treated plant biomass within the primary reactor vessel and for the partially treated plant biomass to be circulated within the reactor vessel through a draft tube through which gas saturated material is directed from the reactor base upwardly and a downward tube through which partially treated biomass flowing from an outlet to the draft tube is returned to the reactor base.

The invention also extends to a method for screening, selecting and isolating biofilm forming bacteria or bacterial consortia that generate high levels of hydrogen from plant biomass or from soluble hydrolysates derived from the hydrolysis of cellulosic materials including hemicellulose said method comprising the following steps:
a) creating a bed of bacteria, in a primary reactor vessel of a fluidized bed bioreactor as described above for producing hydrogen from plant biomass, from a particulate material bed overlaid with activated carbon particles;
b) introducing a mixed consortium of bacteria into the primary reactor vessel;
c) introducing a treated plant biomass into the primary reaction vessel of the reactor; and
d) isolating biofilm forming thermophilic bacteria or bacterial consortia from the particulate material of the bed.

There is further provided for the bed to be a fluidised bed, alternatively a settled bed, further alternatively a, expanded bed and, in the case of a fluidised bed, for recycled gas from the secondary reactor vessel to the primary reactor vessel to fluidize the bed of thermophilic, hydrogen producing bacteria in the primary reactor vessel.

There is further provided for the bacteria to be mesophilic and/or thermophilic bacteria.

There is also provided for the mixed consortium of bacteria to include anaerobic cellulolytic bacteria; for the bacteria making up the mixed consortium to be selected from one or more of a range of mesophylic habitats including primary sewage, soils, compost and rumen dung; and for the thermophilic, hydrogen producing bacteria to be adapted to temperatures ranging from between 20° C. to 80° C. and preferably between 25° C. to 75° C.

There is further provided for the treated plant biomass to be insoluble, preferably cellulosic plant material that has been subjected to only minimum pretreatment being milling and/or wet heating, alternatively for the treated plant biomass to be a soluble hydrolysate derived from hydrolysis of cellulosic material, further alternatively a mixture of insoluble cellulosic material and a hydrolysate derived from hydrolysis of cellulosic material.

There is also provided for the fluidized bed to be formed by a particulate material bed overlaid with activated carbon particles and for the particulate material of the bed to be formed by one or more of steel balls, gravel, glass beads, coal ash particles and the like.

BRIEF DESCRIPTION OF SPECIFIC EMBODIMENTS OF THE INVENTION

Figure 2:
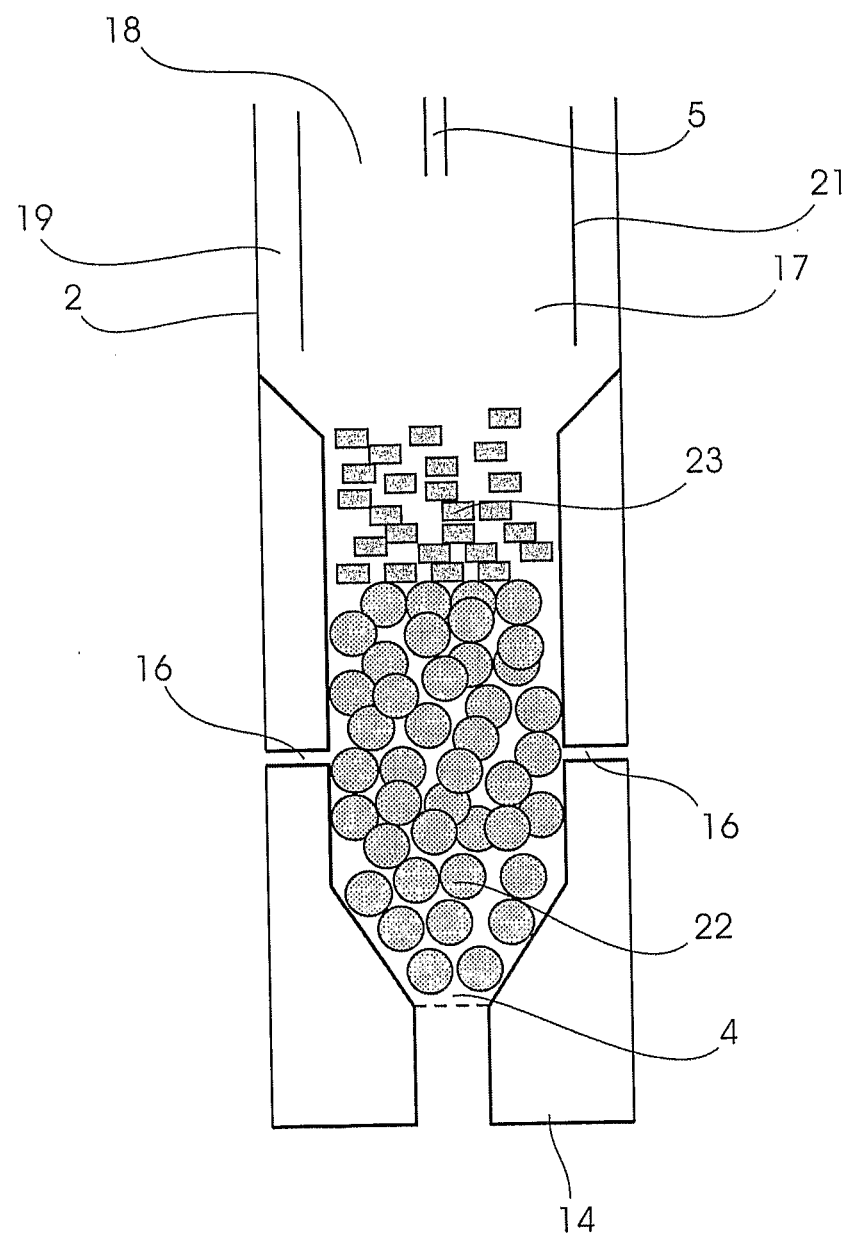

Embodiments of the invention will be described below with reference to the accompanying drawings in which:

FIG. 1 is a schematic sectional side view of one embodiment of a fluidized bed bioreactor according to the invention for producing hydrogen from plant biomass; and FIG. 2 is a detailed schematic side view of the base of the primary reactor of the fluidized bed reactor of FIG. 1.

DETAILED DESCRIPTION OF SPECIFIC EMBODIMENTS OF THE INVENTION

Referring to the figures, a fluidized bed bioreactor (1) for producing hydrogen from plant biomass comprises a circular cylindrical primary reactor vessel (2) having a fluidized bed (3) of hydrogen producing bacteria towards its base (4). The primary reactor vessel (2) has a plant biomass inflow conduit (5) and a pair of treated plant biomass effluent outflow conduits (6) towards an operatively upper end (7) of the vessel (2). The primary reactor vessel (2) in the embodiment illustrated is located within a circular cylindrical secondary reactor vessel (8) and the treated plant biomass effluent outflow conduits (6) discharge into the secondary reactor vessel (8).

The secondary reactor vessel (8) has a conical top (9) which serves as a collector of hydrogen gas produced in the primary reactor vessel. Collected hydrogen gas is led from the reactor (1) by a gas discharge conduit (10). The secondary reactor vessel (8) also has a conical base (11) and, in use, treated plant biomass is drawn from the base of the secondary reactor vessel (8) and is recycled through a recycling conduit (24) by a recycling pump (12) into an inlet (13) at the base (14) of the primary reactor vessel (2).

In the secondary reactor vessel (8) treated plant biomass from the primary reactor vessel is clarified into a first fraction which is drawn from the reactor vessel (8) through a conduit (15) for further processing if required and a second fraction which contains much of any particulate matter in the treated effluent and which settles towards the bottom of the second reactor vessel (8). The second fraction is recycled as described above. Also in the secondary reactor vessel (8) hydrogen gas is released and is collected as described above however, the concentration of hydrogen gas remaining in solution in the treated effluent is sufficient to saturate the effluent which, it is envisaged, enhances the formation of hydrogen gas in the primary reactor vessel (2) as described below.

The primary reactor vessel (2) also has a pair of inorganic nutrient feed conduits (16) which introduce inorganic nutrients into the base of the vessel (2) to promote and, where necessary, sustain the growth of bacteria in the primary reactor vessel (2).

The primary reactor vessel also has a circulation means (17) for circulating partially treated plant biomass within the reactor vessel (2). The circulation means (17) is in the form of a draft tube (18) through which gas saturated material is directed from the reactor base upwardly and a downward tube (19) through which partially treated biomass flowing from an outlet (20) to the draft tube is returned to the reactor base. In this embodiment the draft tube (18) and downward tube (19) are concentric and are formed by a circular cylindrical partition (21) in the reactor vessel (2).

The thermophilic, hydrogen producing bacteria is a mixed consortium of mesophylic bacteria that includes anaerobic cellulolytic bacteria. In use, the bacteria making up the mixed consortium are selected from one or more of a range of mesophylic habitats including primary sewage, soils, compost and rumen dung and they are adapted to temperatures ranging from 25° C. to 75° C.

The thermophilic, hydrogen producing bacterial consortium forms a biofilm in the bed which is formed by a particulate material bed (22) overlaid with activated carbon particles (23). The particulate material of the bed (22) is formed by one or more of steel balls, gravel, glass beads, coal ash particles and the like.

It is also envisaged that the treated plant biomass is an insoluble cellulosic plant material that has been subjected to only minimum pretreatment being milling and/or wet heating. Alternatively the treated plant biomass can be a soluble hydrolysate derived from hydrolysis of cellulosic material or it can be a mixture of insoluble cellulosic material and a hydrolysate derived from hydrolysis of cellulosic material.

The above-described embodiment of the invention will now be described below.

It has been found that the hydrolysis of cellulosic materials and the generation of hydrogen from the products of this hydrolysis becomes increasingly favourable under the action of a mixed consortium of bacteria that includes anaerobic cellulolytic bacterial species. Therefore this bioreactor system includes within its general operation processes that induce the adaptation, isolation, selection and maintenance of mixed anaerobic cellulolytic hydrogen producing consortia. The species making up this mixed consortium were derived from mesophilic habitats including primary sewage, soils, compost and rumen dung. By applying a high dilution rate with partial effluent recycle within the above-described bioreactor, anaerobic cellulolytic hydrogen producing consortia derived from a mixture of inocula which have been obtained from a variety of mesophilic habitats can be rapidly selected and acclimatized or adapted to temperatures from ranging from 25° C. to 75° C.

In addition, the design of the bioreactor allows the bioreactor to be operated in manner which promotes the rapid induction, growth and development of various forms a mixed species bacterial associations. For example the design and operation of the bioreactor rapidly, within four to ten days, facilitates one or more of substrate attached and/or self-attached bacterial forms of multi-species bacterial associations to occur. These two forms of bacterial attachment result in the formation of:

a) mixed specie bacterial biofilms on carrier particles which may be inorganic or organic; or
b) self-attachment of bacteria resulting in the formation of bacterial granules that withstand disintegration under agitation or bacterial flocs that disintegrate readily under agitation.

The bioreactor can be operated such that depending on the nature of the substrate for hydrogen generation, the bacterial may be organized into either, one of or a combination of several of the following types of multispecies associations:

a) granules;
b) flocs;
c) or biofilm attached to a carrier; or
d) or a heterogenous combination of granules, flocs, biofilm and planktonic forms of bacterial associations.

Included in this heterogenous bioreactor system are two kinds of cellulose degrading enzyme systems:

a) external cellulases that have been excreted by the bacteria; and
b), non-excreted cellulases that are attached to the cellulosome complex of the clostridial group of bacteria and their relatives.

Under the action of these two cellulolytic systems rapid hydrolysis of cellulosic materials take place. A 25 to 50 ml effluent sample collected from the bioreactor into Schott bottle was observed to digest completely a 5.0 cm Whatman No 1 filter disc within 24 h at temperatures ranging from 50° C. to 70° C. The development of the heterogenous fluidized bed with this capacity could be induced and developed within 5 days using a mixture of soil, compost, rumen manure and sewage as a source of inoculum.

The design and operation of this bioreactor system facilitates high volumetric biohydrogen productions rates, which depending of substrate materials, range from >100 mmol $H_2/(L.h)$ for insoluble cellulosic materials to between 150 and 290 mmol $H_2/(L.h)$ for soluble substrates which are the breakdown products of cellulose hydrolysis (cellulose derived hydrolysates). The high volumetric biohydrogen production rates are facilitated by the following conditions which are made possible by the design and operation of the bioreactor system: a) maintenance of high bacterial biomass density ranging which depending on substrate can range between 20 and 40 g/L; b) high $H_2$ recovery through gas slipping by recycling $H_2$ saturated effluent back through bioreactor through a bed of materials that facilitate gas bubble formation through cavitation and gas nucleation; c) bioreactor bed expansion and fluidization through the lifting forces generated as a consequence of hydrogen and carbon dioxide gas bubble production at the bottom of the bioreactor; d) rapid material mixing and mass transfer processes facilitated by the gas bubble uplift and internal recycling that takes place within the bioreactor via the central bubble column or draft tithe and the external down-corner tube surrounding the central draft tube. This mixing of the bioreactor contents takes place independently off the external energy consumption or the application of mechanical agitation. Highly efficient dissolved hydrogen and liquid trapped hydrogen is facilitated by hydrogen gas stripping via hydrogen gas bubble formation and bubble size expansion in the bioreactor. While hydrogen is highly insoluble in water, a large quantity of hydrogen remains trapped in the liquid in the form of microscopic bubbles. Highly efficient gas liquid disengagement is promoted by the formation large bubbles which rupture at the liquid surface at the top of bioreactor and rupture as the effluent flows over the sides of the bioreactor into the decanter surrounding the bioreactor or connected to the bioreactor. The flow of the effluent down the sides of the bioreactor vessel into the decanter also induces material mixing and gas-liquid disengagement within the decanter.

In most bioreactor systems low HRTs (or dilution rates) and high influent upflow velocities which are necessary for high biohydrogen production rates are incompatible with the maintenance of high microbial biomass densities within the bioreactor. Usually low HRT and high influent upflow rates results in bacterial biomass depletion through cell washout. With this bioreactor system it has been observed that high organic loading rates associated with low HRT or high dilution rates give higher volumetric hydrogen production rates if the upflow velocity with the bioreactor is increased. The upflow velocity is directly proportional to the effluent recycle rate from the decanter's reservoir into back into the bioreactor. As the upflow velocity or recycle flow rate is increased there is dramatic increase in:
a) the bubble production rate at the bottom of the draft tube within the bioreactor; and
b) the volumetric hydrogen production rate.

This high volumetric hydrogen production associated with high organic low rates (low HRT) and high recycle rates was possible without a corresponding decline in the bioreactor's bacterial biomass density as consequence of excessive cell or granule washout. The internal flow between draft tube and down-corner within the bioreactor together with the expanded diameter of the bioreactor tube at the top of the bioreactor reduced bacterial biomass loss due to washout. In addition, the recycling of effluent from the decanter back into the bioreactor results in the re-inoculation of the bioreactor with seed granules. Granule loss from the bioreactor occurs through two processes: a) small granules (<1.0 mm) have low settling velocities and are washed out has HRTs are decreased and recycle rates in creased; and b) as granule growth and development takes place within the bioreactor the increase in the bed size results in granule washout into the decanter. These two processes result in the collection of granular material in the bioreactor's decanter. This material undergoes further growth and development resulting in additional granule production. These granules within the decanter also generate hydrogen gas and thereby maintain saturated levels of dissolved hydrogen and trapped microscopic hydrogen bubbles within the effluent that is recycled back into the bioreactor. When the effluent is recycled back into the bioreactor at high recycle rates large bubble formation (>1.0 mm) occurs due to cavitation within the particle bed covering the bioreactors bottom recycle inlet. Cavitations are transformed into stable gas filled bubbles as dissolved hydrogen diffuses into the cavitation, in addition, the microscope bubbles coalesce with the cavitations. The bubbles grow in size and number and reduce the density of the liquid in the draft tube. As a consequence of bubble formation work is done on the liquid and the granules in the draft tube resulting in the fluidization of the granular bed and the recycling of material within the bioreactor via the draft and down-corner tubes. This process enhances mixing and mass transfer within the bioreactor thereby increasing the volumetric reactivity of the bioreactor with regard to substrate transformation into biohydrogen and new microbial biomass.

It is also envisaged that under conditions where the concentration of the organic substrate supply is low the bioreactor design allows for the high nutrient influent rates and high effluent recycle rates. This will facilitate a high volume throughput of nutrient supplies that have low organic concentrations.

The above-described bioreactor also results in a rapid induction of biofilm, bacterial granules and bacterial floc. Many theories have been put forward to explain to the bacterial granulation or flocculation process. It appears that the factors which are conducive for bacterial granulation initiation in the bioreactor system described in this patent involve pH and biofilm formation. Biofilm growth and development results in the formation of granulation nuclei on the surface of the biofilm. As pH within the bioreactor falls below 6.0 visible formation of biofilm becomes apparent on the surface of the particulate material at the base of the bioreactor. This particulate material (>4.0 mm) may be glass, plastic, stainless steel, coal ash, gravel. Also on the surface of the layer of activated carbon particles (3 mm diameter, 6 to 10 mm long) the formation of biofilm becomes apparent. Shearing of the granulation nuclei from the biofilm layer supplies the bioreactor with clumps of self-attached bacteria that act as seed material for the growth and development granules. At low recycle rates and decreasing HRTs (increasing organic loading rates) the growth and development of granules proceeds from the surface of the expanded bed of activated carbon. Small granules that are washed out from the collector are trapped in the decanter where they continue undergo further growth and development before been recycled back into the bioreactor. In this invention full bioreactor bed granulation occurs within 3 to 10 days. Other factors that promote rapid granulation include:
a) direct injection of nutrient into the bed of particulate material via the multiple horizon nutrient inlet ports; and
b) gas bubble induced expansion of the layer of activated carbon overlaying the particulate material.

In use, fluid passing through the fluidised bioreactor (2) decants over the sides of this bioreactor and is collected into the clarifier in the outer larger vessel (8). The effluent flowing down the sides on the bioreactor vessel (2) acquires kinetic energy which causes material mixing and bubble formation in the upper surface of the fluid contained in the larger decantor vessel (8), the upper half of which is used for gas collection and the lower half of which functions as a clarifier.

The entire system is gas tight so that gas can only escape from the system through the gas vent (10) for hydrogen gas collection. Consequently the entire bulk liquid or aqueous phase of the bioreactor, piping and decanter is maintained in a carbon dioxide and hydrogen gas saturated state. The gas component in the liquid phase occurs in two forms:
a) dissolve gas, and
b) microscopic gas bubbles trapped within the liquid phase.

Gas saturated effluent (containing dissolved gas and entrapped microscopic bubbles) is recycled from the decanter into the base of the bioreactor through a bed of particulate material overlaid with activated carbon particles. The particulate material may be comprised of material such as steel balls, gravel, glass bead, coal ash and so on. The particulate material promotes cavitation of the liquid phase as the fluid is pumped in an upwardly direction through the bed of particulate material. Cavitation collapse is prevented by:
a) the diffusion of dissolved gas into the cavity; and
b) coalescence of microscopic bubbles with the cavity.

These two processes result in the formation of bubbles. The upwardingly moving bubbles expand in size and perform lifting work on:
a) the layer of activated carbon particles overlying the bed of particulate material, resulting in the bed expansion;

b) the fluid in the draft tube; and
c) the bacterial granules in the draft tube.

Expansion of the bed of activated carbon particles increases bed porosity which in turn promotes, as a consequence of improved nutrient flow through the bed, the growth of biofilm and development of granule nuclei.

Further, as the gas hold up in the liquid phase increases in the draft tube due to bubble formation, the gas filled less dense fluid raises upward in the bioreactor draft tube. This upflow of fluid in the draft tube fluidizes the bioreactor bed which may be comprised of granules or flocs or insoluble particulate cellulosic materials. The fluidized bioreactor bed may also be heterogeneous consisting of a mixture of bacterial granules, bacterial flocs and biofilm coated particles of cellulosic materials. In the heterogeneous fluidized bed the material becomes classified according to density within the draft tube. The upward velocity of low density particles rapidly declines within the expanded diameter of the upper part of the draft tube. This prevents the escape of a large fraction of the less dense material from the bioreactor into the decantor. The less dense material is carried downward in the sinking dense fluid within the down corner tube. The lighter and smaller bacterial granular particles or bacterial flocs that are washed out into the decanter undergo an increase in size due to further growth and development in the decanter. They are then recycled as increased sized particles back into the bioreactor.

In addition, liquid-gas disengagement at the top of the bioreactor is promoted with the rupture of large gas bubbles at the surface of the liquid at the top of the bioreactor. Additional liquid-gas disengagement occurs with the release of gas from smaller bubbles and microscopic bubbles as the fluid decants over the side of the bioreactor into the decanter. With the transfer of kinetic energy by the fluid flowing down the sides of the bioreactor into the upper surface of the fluid in the decanter results in the further creation of bubbles, thereby promoting further liquid-gas disengagement within the decanter vessel It is envisaged that this invention involves the application of a bioreactor-decanter-clarifier-gas separator/collector (BDCG) assembly and each of these concepts together with their mode of operation is described as follows:

1. A chemostat that facilitates the rapid selection, growth and development of hydrogen producing anaerobic thermophilic cellulolytic multispecies bacterial consortiums. In this application the concept of a chemostat is defined as any bioreactor that is always operated at dilution rates greater than the maximum specific growth rate of the bacterial species in the bioreactor. Only bacterial cells that are organized into attached multispecies assemblies which exist as particulate structures with good settling properties will be maintained in the bioreactor. These particulate structures may exist in the form of biofilm attached to some carrier substrate or as self-attached assemblies in the form of bacterial granule or flocs. Various potential or suitable biofilm carrier substrates may be used such as biolite, even as a mixture with insoluble cellulosic particulate material. The continuous operation of the bioreactor as a chemostat facilitates therefore not only the rapid selection of hydrogen producing anaerobic cellulolytic bacteria from a diversity of mesophilic habitats such a sewage, soil, compost or rumen manure, but also selects from these bacteria species that can become adapted or acclimatized to increasingly higher temperatures, that is, temperatures within the 50° C. to 75° C. range.

2. A system that promotes the rapid formation and long-term maintenance of bacterial particulate structures with good settling properties. Depending on whether the feedstock is insoluble cellulosic materials or soluble cellulose derived hydrolysates, the bacterial consortium may be immobilized as attached biofilms or immobilized as self-attached associations in the form of granules or flocs. Or alternatively, all three forms of immobilized bacterial consortium structures may co-exist stably within the same bioreactor. These 3 forms of immobilized bacterial consortium association result in the formation of particulate structures that have good settling properties. Bacterial immobilization results in the formation of a particulate structure consisting of any of the following: a) a multi-cell bacterial complex that is attached as a biofilm to a particulate carrier substrate, or b), a self-attached multi-cell bacterial complex existing in the form of granule or floc. This embodiment of the BDCG assembly facilitates the rapid induction, growth, development and long-term maintenance of bacterial particulate structures with good settling properties. Rapid initiation of the formation microscopic multi-cellular self-attached bacterial clusters into pre-granule or pre-floccular nuclei is facilitated by the following combination of factors. Rapid production of these microscopic multi-cellular self-attached bacterial clusters requires the formation of bacteria biofilm on carriers in the presence of a strong shear field under conditions where both the rate of nutrients supply and nutrient mass transfer is non-limiting. These conditions are achieved in the bioreactor by:

a) direct injection of nutrients into bed of inert particulate material (>4 mm in cross-section) overlaid by an expanded bed of activated carbon particles, and
b) recycling effluent from the decanter through the this bed of material. The nutrients are injected into the bed via a system of a multiple-inlet ports that are orientated perpendicular to the vertical-axis of the bioreactor.

Following the initial inoculation of the bioreactor with the bacterial inoculum, the bioreactor is first operated in a batch re-cycle mode for between 24 and 48 h, before been switched to continuous re-cycle mode. After switching to the continuous re-cycle mode the nutrient flow rate and the upflow velocity are increased in a step-wise fashion over 4 to 10 days. Over this period an expanded bed of granules forms above the bed of activated carbon particles. Rapid growth and development of the fluidized bacterial granular bed is promoted by the following sequence of events: a) Initiation and growth of attached biofilm in a field of high shear forces. b) Detachment of pre-granule multi-cellular nuclei from the biofilm by the action of shear forces resulting in the formation of suspended microscopic self-attached multi-cellular bacterial granule precursors. c) Growth and development of suspended multi-cellular microscopic bacterial clusters (<1 mm) into macroscopic bacterial granules (>1 mm) within the bioreactor and decanter. d) Microscopic bacterial granules that are washout from the bioreactor into the clarifier undergo further growth and development in the clarifier. These are then re-cycled back into the bioreactor through the particulate bed at the bottom of the bioreactor. Their passage through the particulate bed at high fluid velocities in the presence of massive bubble production exposes them to the action of high shear forces. Under these conditions the granules are fragmented into smaller sized particles. This results in the bioreactor being continuously re-seeded with a supply of bacterial granule precursors. Low HRTs, high organic loading rates, and high effluent re-cycle velocities, facilitate the rapid growth and development of a dense fluidized granular bed under conditions that are essentially chemostatic.

3. The bioreactor system contains two material re-cycling systems:
   a) The actual bioreactor itself contains an internal material recycling system consisting of an up-flow or draft-tube surrounded by a down-flow or down-corner tube, and
   b) the bioreactor in turn is associated with a second external material re-cycling system which is the clarifier.

The bioreactor can either be contained within a larger vessel functioning as the clarifier or the bioreactor may be connected with a separate vessel functioning as a clarifier. The clarifier is multifunctional vessel which has the following functions:
   a) it functions as a trap for microscopic bacterial granular material washed-out from the bioreactor;
   b) it functions as a culture vessel for the growth and development of microscopic granules into macroscopic granules; and
   c) it functions as vessel for the generation of effluent which is saturated with dissolved hydrogen gas and trapped microscopic gas bubbles.

The bioreactor vessel also functions as a decanter which discharges effluent over its sides into the surrounding clarifier or via a connecting pipe to an external clarifier. In both cases the effluent discharged from the top opening of the bioreactor acquires kinetic energy as it flows into the clarifier. This results in a transfer of kinetic energy into the upper layers of the decanter which promotes mixing and suspension of micro-sized bacterial granular particles. In addition the transfer of kinetic energy into the upper layers of the clarifier cause macro-bubble formation and hydrogen gas escapes from the fluid surface of the clarifier. As the granules grow in the clarifier they settle to the bottom of the clarifier and are pumped back into the bioreactor.

4. The bioreactor configuration consists of a fluidized bed bioreactor contained within a larger vessel that functions both as a gas separator and clarifier and is more efficient with regard to hydrogen recovery and substrate recycling. In such a setup, the fluid passing through bioreactor would decant over the sides of the bioreactor and would be collected into the clarifier surrounding the bioreactor. This arrangement of a bioreactor that is designed to allow the effluent to decant over the sides will increase gas-liquid separation. The upper half of the vessel containing the bioreactor will be conical shaped for gas collection and the lower half will be conical shaped to function as a clarifier. Such a system would combine the bioreactor-decanter-clarifier-gas separator into a single process operational unit. This would decrease plumbing complexity and increase ease of bioreactor process operations. It will also increase hydrogen gas recovery.

5. Hydrogen gas stripping from the bioreactor by means of hydrogen gas generated from endogenous hydrogen gas production within the clarifier. High upflow fluid velocities through the particulate bed as the base of the bioreactor using clarifier derived effluent results in the generation of hydrogen gas bubbles within the particulate bed which turn perform two functions within the bioreactor:
   a) hydrogen gas bubble generation at the base of the draft-tube drives fluid and material flow up the draft-tube, and with the escape of bubbles from the upper surface of the bioreactor vessel, the more denser fluid sinks to the bottom of the bioreactor via the external down-corner tube; and
   c) hydrogen gas is stripped from the bioreactor aqueous phase through gas diffusion into bubbles and through bubble coalescence.

6. It is envisaged that the bioreactor-decanter-clarifier-gas separator/collector (BDCG) assembly can be used for the anaerobic production of hydrogen from insoluble lignocellulosic substrates and from soluble hydrolysates (disaccharides, hexoses and pentoses) derived from the hydrolysis of cellulosic materials. In the case of insoluble lignocellulosic materials the BDCG assembly is operated as follows. The bioreactor with contain a heterogenous fluidized bed consisting of the following components: a pulp bed of cellulosic materials; mixed bacterial consortium attached as biofilm to cellulosic particles; bacterial granules and bacterial flocs. The bioreactor will contain bacteria that have attached cellulases in the form of cellulosomes. The bacteria will be attached to cellulosic particles. In addition to the above cellulolytic bacteria, the bioreactor will also contain other cellulolytic microorganisms that excrete cellulases into the surrounding fluid bulk phase. Hence the bioreactor will contain two cellulolytic systems. In addition to the re-cycling of effluent from the clarifier into the bioreactor, effluent from the clarifier will also be mixed with the lignocellulosic material before it enters the bioreactor. Before being loaded into the bioreactor the lignocellulosic material or plant biomass will be dry milled and enriched with wheat bran. The material then be mixed with the effluent from the clarifier and then wet milled to further reduce the particle size of the material and converting it to a pulp slurry. The pulp slurry will be stored in feed tank from which the pulp slurry will be pumped into the bioreactor of the BDCG assembly. Prior to its being pumped into the bioreactor the pulp slurry will have undergone the following pretreatment: a) Hydrolysis as a consequence of exposure to cellulases in the effluent from clarifier; b) inoculation with cellulolytic bacteria. The remaining balance of the effluent from the clarifier which will contain soluble hydrolysates will be used as the feedstock for hydrogen production in a second bioreactor-decanter-clarifier-gas separator/collector (BDCG) assembly.

7. Generation of methane with the bioreactor-decanter-clarifier-gas separator/collector (BDCG) assembly. The effluent from the BDCG system that has been supplied with soluble substrates in the form of hexoses and pentoses will generate acetate as one of the end products. The remaining balance of the effluent from the clarifier which contains high concentrations of acetate will be used as the feedstock for methane production in a methane producing BDCG assembly. The methane produced may be reformed to give hydrogen or combusted for steam production.

Methodology:

This invention involves the application of the chemostat methodology towards the selection of biofilm, bacterial flocs, and bacterial granule forming thermophilic bacterial consortia that can generate hydrogen from biomass derived hydrolysates and from insoluble cellulosic materials. The chemostat bioreactor consists of fluidized bed containing suitable particles such as granulated activated carbon/charcoal (GAC) on which bacteria can attach and grow to form biofilm. The activated carbon particles overlay larger inert particles which are involved in bubble formation through the process of cavitation. This bioreactor apparatus can be used as a chemostat for the selection biofilm forming or granule forming hydrogen generating thermophilic bacterial consortia. It can also be readily scaled up into a process plant for the commercial production of hydrogen from plant biomass. The methodology can also be adapted and applied at the level of the full process plant scale.

This methodology and bioreactor can be used to facilitate the rapid screening and selection of suitable thermophilic bacteria or bacteria consortia for hydrogen production from plant biomass. Implementation of the chemostat methodology allows for the screening, selection and isolation for culturing of biofilm forming consortia of hydrogen generating thermophilic bacteria directly in or from the bioreactor as the case maybe. In this strategy a bioreactor-decanter-clarifier-gas separator/collector is used as a chemostat for screening and selecting thermophilic bacteria that readily form biofilms on GAC particles. The design and operation of the bioreactor results in the stripping of hydrogen via the purging of the bioreactor with endogenously produced hydrogen gas bubbles. Because the liquid phase of the bioreactor is always saturated with dissolved hydrogen there will always be net movement of hydrogen from the liquid phase into the gaseous phase with bubbles. This highly efficient and rapid partitioning of hydrogen into gaseous phase from the liquid-dissolved soluble phase shifts the equilibrium for hydrogen generation at the molecular-cellular level in the forward direction.

In the methodology very large samples containing possible thermophilic inoculum can be readily applied directly to the bioreactor. Samples can collected from a range of different ecological niches that have a high probably of been enriched with cellulolytic anaerobic thermophilic bacterial communities. Large samples ranging from 100 g to 1 kg of sample material will be prepared so that it can be directly inoculated into the bioreactor. After inoculation the bioreactors will be operated in recycle-batch mode using a selected media that will facilitate the growth of consortia bacteria that can either utilize only biomass hydrolysates ($C_5$ and $C_6$ sugars) or cellulosic substrates. One day after bioreactor inoculation the temperature will be gradually increased over the next 2 days from 37° C. to 70° C. to select extreme thermophiles. After this period the bioreactor is switched to continuous mode and the dilution rate will be gradually increased until in combination with re-cycle flow velocity the total up-flow rate through the bioreactor particulate material bed will be between 5.2 and 10 m/h. As the dilution rate is increased all key bioreactor variables are monitored such as: influent substrate concentration, effluent substrate concentration, organic acids in the effluent, pH, ORP, temperature, conductivity, turbidity, $CO_2$, $H_z$, and planktonic bacterial OD. This is done so has to rapidly assess the hydrogen production potential of the bacterial biofilm, bacterial granule and bacterial floc that has been generated in the bioreactor bed from the sample containing the original inoculum. Biofilm, granule or floc growth can be monitored by recording settled bed height. It is expected that the rate of hydrogen production will increase as dilution rate increases or HRT declines. Should this scenario prevail for both types of substrates, i.e., biomass hydrolysates or cellulosic substrates, then within 4 to 10 days a thermophilic hydrogen generating biofilm or bacterial granule consortium will have become established in the bioreactor. For each constant dilution rate a steady-state with respect to bioreactor variables and biofilm bacterial consortium species composition will be attained. For each steady-state, samples of biofilm or bacterial granules will be removed from the bioreactor bed to culture and identify bacteria.

Further Application of the Bioreactor-Decanter-Clarifier-Gas Separator/Collector (BDCG) Assembly.

In addition to hydrogen production, the above invention can be also used as an application for the production of solvents such as ethanol, butanol, propanol, acetone from a diversity of organic substrates such as glycerol and cellulose for example.

1. Acetone, butanol, and ethanol are solvents which are co-generated with hydrogen in the BDCG system. Continuous production and recovery of acetone-butanol-ethanol (ABE) through gas-stripping in a BDCG assembly. The invention was extended in its application to continuous ABE production. In general the BDCG involving a fluidized bed of bacterial biofilm attached to a carrier or a fluidized bed of bacterial granules can be used to generate ABE solvents and to recover the solvents by gas stripping. In one particular ABE application the BDCG assembly was tested with for its capacity to generate ABE solvents and recover these solvents through gas-stripping and condensation. The test application involved a fluidized granular bed in a bioreactor with an internal recycle gas-lift loop, gases consisting of $H_2$ and $CO_2$ that were endogenously produced by recycling gas saturated effluents at high flow rates through the particulate bed situated at the bottom of the bioreactor. In the test application two nutrient media were evaluated: Endo medium with 20 g sucrose/L as the nutrient source and Endo medium with 20 g/L of finely wet homogenized wheat bran. It was observed that as HRTs were reduced to 0.5 h and the effluent recycle rates were increased to 5.5 m/h for a BDCG assembly with a total volume of 7.5 L (bioreactor plus clarifier), the gas flow through the draft-tube increased to 90 L/h. The gas escaping from the bioreactor was passed through a condenser. Acetone, ethanol, butanol, propanol were detected in the condensate. This was achieved for both types of Endo medium. The achievement of the high rates of endogenous gas production necessary for the gas-stripping of ABE solvents, it necessary to have bioreactor bacterial densities greater than 30 g/L. These bacterial mass densities with bioreactors are only possible in case of fluidised bacterial granular bed bioreactors. Maintenance of bacterial mass densities in excess of 40 g/L in the form of a fluidized bacteria granular bed within the BDCG was readily achievable in the BDCG assembly. Using inoculum derived from a mixture of rumen manure and sewage, granules comprised of a mixed bacterial consortium that included clostridial species were induced in the bioreactor. Using 16S rDNA PCR and density gradient gel electrophoresis (DGGE) the presence of the following species in the bacterial granules were confirmed: *C. cellobioparum, C. butyricum, C. acetylbutylicum, C. pasteurianum, C. perfringens*.

2. Continuous production of ethanol from glycerol through gas-stripping in a BDCG assembly. This application a fluidized granular bed comprised of a mixed consortium of mesophilic facultatively anaerobic bacterial were supplied with Endo medium supplemented with 20 g/L glycerol. The HRT was reduced to 0.5 h and the effluent recycle rates were increased to 5.2 m/h for a BDCG assembly with a total volume of 7.5 L. The gas flow rate through the draft-tube increased to 74 L/h. The gas escaping from the bioreactor was passed through a condenser. Ethanol was detected in the condensate.

Laboratory studies performed by the inventor using a bench-scale prototype with a total operating volume of 7.5 L the bioreactor-decanter-clarifier-gas separator/collector (BDCG) assembly has been operated at the following HRTs times: 8 h, 6 h, 4 h, 3 h, 2 h, 1 h and 0.5 h have yielded the following results:

1. With Endo medium supplemented with 17.5 g/L of sucrose the bioreactor gave a volumetric biohydrogen production rate of between 200 and 290 mmol $H_2$/(h.L) at a mesophilic temperature of 40° C. as the HRT was reduced to 0.5 h for a BDCG assembly with a total working volume of 7.5 L. The ratio of $H_2$ to $CO_2$ rates from 42.6% to 51%. The bacteria biomass density as the HRT was reduced to 0.5 h increased to 40.0 g/L. The gas flow rate in the draft tube increased to 94 l/h. Application of 16S rDNA PCR and density gradient gel electrophoresis (DGGE) confirmed the presence of the following species in the bacterial granules: C. butyricum, C. acetylbutylicum, C. pasteurianum, C. perfringens. Bacterial inoculum was derived from a mixture of soil, rumen manure and sewage 2. With Endo medium supplemented with 17.5 g/L of sucrose the bioreactor gave a volumetric biohydrogen production rate of between 100 and 200 mmol $H_2$/(h.L) at a thermophilic temperature of 60° C. as the HRT was reduced to 0.5 h. The gas flow rate in the draft tube increased to 90 L/h. Bacterial inoculum was derived from a mixture of soil, compost, rumen manure and sewage.

3. Using an Endo medium where the sucrose was replaced with wheat bran at a concentration of 20 g/L, the bioreactor gave a volumetric biohydrogen production rate of 150 mmol $H_2$/(h.L) at a thermophilic temperature of 60° C. for a HRT of 4 h. A heterogenous fluidized bed consisting of biofilm coated bran particles, bacterial granules and bacterial flocs was formed in the bioreactor. Bacterial inoculum was derived from a mixture of soil, compost, rumen manure and sewage.

4. With Endo medium supplemented with 17.5 g/L sucrose the bioreactor gave a volumetric methane production rate of between 150 mmol $H_2$/(h.L) at mesophilic temperatures at a HRT of 0.5 h.

The invention claimed is:

1. A bioreactor for producing hydrogen from plant biomass, the reactor comprising a primary reactor vessel having a bed of hydrogen producing bacteria towards its base, a plant biomass inflow, a treated plant biomass effluent outflow towards its operatively upper end, and a gas saturated plant biomass effluent recycle inlet into the bed, and a secondary reactor vessel having a treated plant biomass effluent inlet from the primary reactor vessel, a gas outlet and a gas saturated plant biomass effluent recycle outlet, the gas saturated plant biomass effluent recycle outlet leading to a recirculation pump which, in use, recycles gas saturated plant biomass effluent from the secondary reactor vessel to the primary reactor vessel.

2. The bioreactor for producing hydrogen from plant biomass of claim 1, wherein the bed is a fluidised bed bioreactor.

3. The bioreactor for producing hydrogen from plant biomass of claim 2, wherein recycled gas from the secondary reactor vessel to the primary reactor vessel fluidises the bed of thermophilic, hydrogen producing bacterial in the primary reactor vessel.

4. The bioreactor for producing hydrogen from plant biomass of claim 1, wherein the bed is a settled bed bioreactor.

5. The bioreactor for producing hydrogen from plant biomass of claim 1, wherein the bed is an expanded bed bioreactor.

6. The bioreactor for producing hydrogen from plant biomass of claim 1, wherein the bacteria are mesophilic and/or thermophilic bateria.

7. The bioreactor for producing hydrogen from plant biomass of claim 1, wherein the recycled plant biomass effluent is saturated with hydrogen gas produced in the primary reactor vessel.

8. The bioreactor for producing hydrogen from plant biomass of claim 1, wherein the bed of hydrogen producing bacteria has at least one inorganic nutrient feed inlet.

9. The bioreactor for producing hydrogen from plant biomass of claim 1, wherein the primary reactor vessel is located within the secondary reactor vessel.

10. The bioreactor for producing hydrogen from plant biomass of claim 9, wherein the secondary reactor vessel has an excess, unrecycled plant biomass effluent outlet.

11. The bioreactor for producing hydrogen from plant biomass of claim 1, wherein the secondary reactor vessel functions, in use, as a clarifier and/or gas separator for treated plant biomass effluent received from the primary reactor vessel.

12. The bioreactor for producing hydrogen from plant biomass of claim 1, wherein the hydrogen producing bacteria is a mixed consortium of mesophylic and/or thermophilic bacteria that includes anaerobic cellulolytic bacteria.

13. The bioreactor for producing hydrogen from plant biomass of claim 12, wherein the bacteria making up the mixed consortium is selected from one or more of a range of mesophylic habitats including primary sewage, soils, compost and rumen dung.

14. The bioreactor for producing hydrogen from plant biomass of claim 1, wherein the hydrogen producing bacteria are adapted to temperatures ranging from between 20° C. and 80° C.

15. The bioreactor for producing hydrogen from plant biomass of claim 14, wherein the hydrogen producing bacteria are adapted to temperatures ranging from between 25° C. and 75° C.

16. The bioreactor for producing hydrogen from plant biomass of claim 1, wherein the treated plant biomass is insoluble.

17. The bioreactor for producing hydrogen from plant biomass of claim 16, wherein the insoluble treated plant biomass is cellulosic plant material that has been subjected to only minimum pretreatment being milling and/or wet heating.

18. The bioreactor for producing hydrogen from plant biomass of claim 1, wherein the treated plant biomass is a soluble hydrolysate derived from hydrolysis of cellulosic material.

19. The bioreactor for producing hydrogen from plant biomass of claim 1, wherein the treated plant biomass is a mixture of insoluble cellulosic material and a hydrolysate derived from hydrolysis of cellulosic material.

20. The bioreactor for producing hydrogen from plant biomass of claim 1, wherein the primary reactor vessel has a base on which the bed is formed in use.

21. The bioreactor for producing hydrogen from plant biomass of claim 20, wherein the bed is formed by a particulate material bed overlaid with activated carbon particles.

22. The bioreactor for producing hydrogen from plant biomass of claim 21, wherein the particulate material of the bed is formed by one or more of steel balls, gravel, glass beads and coal ash particles.

23. The bioreactor for producing hydrogen from plant biomass of claim 22, wherein the particulate material of the bed is coated with a biofilm formed from a mixed consortium of thermophilic and/or mesophylic bacteria.

24. The bioreactor for producing hydrogen from plant biomass of claim 1, wherein the primary reactor vessel has a circulation means for circulating partially treated plant biomass within the reactor vessel.

25. The bioreactor for producing hydrogen from plant biomass of claim 1, wherein the circulation means comprising a draft tube through which gas saturated material is directed from the reactor base upwardly and a downward tube through which partially treated biomass flowing from an outlet to the draft tube is returned to the reactor base.

26. A method for producing hydrogen from plant biomass comprising the following steps:
   a) introducing a plant biomass into a primary reactor vessel of a bioreactor of claim 1 having a bed of thermophilic and/or mesophilic hydrogen producing bacteria towards its base;
   b) treating the introduced plant biomass with a mixed consortium of hydrogen producing bacteria that includes anaerobic cellulolytic bacteria to produce hydrogen;
   c) transferring the treated plant biomass to a secondary reactor vessel having a treated plant biomass effluent inlet from the primary reactor vessel;
   d) collecting hydrogen gas from the second reactor vessel and clarifying treated plant biomass effluent;
   e) collecting a supernatant from the clarified treated plant biomass; and
   f) recirculating uncollected clarified treated plant biomass to the primary reactor vessel.

27. The method for producing hydrogen from plant biomass of claim 26, wherein the bed is a fluidised bed bioreactor.

28. The method for producing hydrogen from plant biomass of claim 27, wherein recycled gas from the secondary reactor vessel to the primary reactor vessel fluidises the bed of hydrogen producing bacteria in the primary reactor vessel.

29. The method for producing hydrogen from plant biomass of claim 26, wherein the bed is a settled bed bioreactor.

30. The method for producing hydrogen from plant biomass of claim 26, wherien the bed is an expanded bed bioreactor.

31. The method for producing hydrogen from plant biomass of claim 26, wherein the recycled plant biomass effluent is saturated with hydrogen gas produced in the primary reactor vessel.

32. The method for producing hydrogen from plant biomass of claim 26, further comprising: introducing at least one inorganic nutrient feed into the bed of hydrogen producing bacteria.

33. The method for producing hydrogen from plant biomass of claim 26, further comprising: circulating partially treated plant biomass within the primary reactor vessel.

34. The method for producing hydrogen from plant biomass of claim 33, wherein the partially treated plant biomass is circulated within the reactor vessel through a draft tube through which gas saturated material is directed from the reactor base upwardly and a downward tube through which partially treated biomass flowing from an outlet to the draft tube is returned to the reactor base.

35. A method for screening, selecting and isolating biofilm forming mesophilic and/or thermophilic bacteria or bacterial consortia that generates hydrogen from plant biomass or from soluble hydrolysates derived from the hydolysis of cellulosic materials including hemicellulose, said method comprising the following steps:
   a) creating a bed suitable for colonization by a mixed consortium of bacteria, in a primary reactor vessel of a bioreactor for producing hydrogen from plant biomass, from a particulate material bed overlaid with activated carbon particles, the bioreactor comprising:
      the primary reactor vessel, a plant biomass inflow, a treated plant biomass effluent outflow towards its operatively upper end and a gas saturated plant biomass effluent recycle inlet into the bed, and a secondary reactor vessel having a treated plant biomass effluent inlet from the primary reactor vessel, a gas outlet and a gas saturated plant biomass effluent recycle outlet, the gas saturated plant biomass effluent recycle outlet leading to a recirculation pump which, in use, recycles gas saturated plant biomass effluent from the secondary reactor vessel to the primary reactor vessel;
   b) introducing a mixed consortium of bacteria into the primary reactor vessel;
   c) introducing a treated plant biomass into the primary reaction vessel of the reactor; and
   d) isolating biofilm forming bacteria or bacterial consortia from the particulate material of the bed.

36. The method for screening, selecting and isolating biofilm forming bacteria or bacterial consortia of claim 35, wherein the mixed consortium of bacteria includes anaerobic cellulolytic bacteria.

37. The method for screening, selecting and isolating biofilm forming bacteria or bacterial consortia of claim 35, wherein the bacteria making up the mixed consortium are selected from one or more of a range of mesophylic habitats including primary sewage, soils, compost and rumen dung.

38. The method for screening, selecting and isolating biofilm forming bacteria or bacterial consortia of claim 35, wherein the hydrogen producing bacteria are adapted to temperatures ranging from 20° C. to 80° C.

39. The method for screening, selecting and isolating biofilm forming bacteria or bacterial consortia of claim 35, wherein the treated plant biomass is insoluble.

40. The method for screening, selecting and isolating biofilm forming bacteria or bacterial consortia of claim 39, wherein the insoluble treated plant biomass is cellulosic plant material that has been subjected to only minimum pretreatment being milling and/or wet heating.

41. The method for screening, selecting and isolating biofilm forming bacteria or bacterial consortia of claim 35, wherein the treated plant biomass is a soluble hydrolysate derived from hydrolysis of cellulosic material.

42. The method for screening, selecting and isolating biofilm forming bacteria or bacterial consortia of claim 35, wherein the treated plant biomass is a mixture of insoluble cellulosic material and a hydrolysate derived from hydrolysis of cellulosic material.

43. The method for screening, selecting and isolating biofilm forming bacteria or bacterial consortia of claim 35, wherein the bed is a fluidized bed.

44. The method for screening, selecting and isolating biofilm forming bacteria or bacterial consortia of claim 43, wherein the particulate material of the fluidized bed is formed by one or more of steel balls, gravel, glass beads and coal ash particles.

* * * * *